United States Patent
Stemmer

(10) Patent No.: US 8,604,786 B2
(45) Date of Patent: Dec. 10, 2013

(54) METHOD AND DEVICE FOR CONTROLLING ACQUISITION OF MAGNETIC RESONANCE DATA IN A MAGNETIC RESONANCE APPARATUS

(75) Inventor: Alto Stemmer, Abenberg (DE)

(73) Assignee: Siemens Aktiengesellschaft, Munich (DE)

( * ) Notice: Subject to any disclaimer, the term of this patent is extended or adjusted under 35 U.S.C. 154(b) by 439 days.

(21) Appl. No.: 12/725,943

(22) Filed: Mar. 17, 2010

(65) Prior Publication Data

US 2010/0237863 A1  Sep. 23, 2010

(30) Foreign Application Priority Data

Mar. 19, 2009 (DE) .......................... 10 2009 014 054

(51) Int. Cl.
*G01V 3/00* (2006.01)
*G01R 33/48* (2006.01)

(52) U.S. Cl.
USPC ........... 324/309; 324/307; 324/318; 324/322; 600/410

(58) Field of Classification Search
USPC ............................ 324/300–322; 600/407–464
See application file for complete search history.

(56) References Cited

U.S. PATENT DOCUMENTS

| | | | |
|---|---|---|---|
| 5,606,258 A * | 2/1997 | Hoenninger et al. | 324/309 |
| 6,888,349 B2 * | 5/2005 | Fautz | 324/309 |
| 7,051,286 B1 | 5/2006 | Stemmer et al. | |
| 7,417,430 B2 * | 8/2008 | Aldefeld et al. | 324/309 |
| 7,443,162 B2 * | 10/2008 | Deimling | 324/307 |
| 7,443,166 B2 * | 10/2008 | Heid | 324/322 |
| 7,782,052 B2 * | 8/2010 | Fishkin | 324/307 |
| 8,085,042 B2 * | 12/2011 | Graessner et al. | 324/307 |
| 2003/0060698 A1 | 3/2003 | Mistretta | |
| 2003/0216637 A1 | 11/2003 | Ho et al. | |
| 2005/0264286 A1 | 12/2005 | Harder | |
| 2005/0264288 A1 | 12/2005 | Campagna et al. | |
| 2006/0184004 A1 | 8/2006 | Machida | |
| 2007/0222442 A1 | 9/2007 | Aldefeld et al. | |
| 2008/0211496 A1 * | 9/2008 | Tanoue et al. | 324/307 |
| 2009/0278535 A1 * | 11/2009 | Takizawa et al. | 324/309 |
| 2010/0189328 A1 | 7/2010 | Boernert et al. | |

OTHER PUBLICATIONS

"Sliding Multislice (SMS): A New Technique for Minimum FOV Usage in Axial Continuously Moving-Table Acquisitions," Fautz, et al., Magnetic Resonance in Medicine, vol. 55 (2006) pp. 363-370.
"MDS-Manual," Department of Diagnostic Radiology, Medical Physics, University Hospital, Freiburg, Germany.

* cited by examiner

*Primary Examiner* — Jermele M Hollington
*Assistant Examiner* — Emily Chan
(74) *Attorney, Agent, or Firm* — Schiff Hardin LLP

(57) ABSTRACT

In a method and a device to control the workflow of an MR measurement in a magnetic resonance system, a predetermined volume segment is subdivided into parallel slices with a predetermined slice interval and measured with a continuous table feed. Apart from a start phase and an end phase of the MR measurement, multiple slices of the examination subject are excited and read out in every repetition of the underlying basic sequence, and these multiple slices are located in an active volume inside the magnetic resonance system. The number of slices excited and read out per repetition of the underlying basic sequence is selected automatically depending in particular on the parameters determining an image contrast and an image resolution, and thus cannot be freely set by a user of the magnetic resonance system.

44 Claims, 3 Drawing Sheets

FIG 1

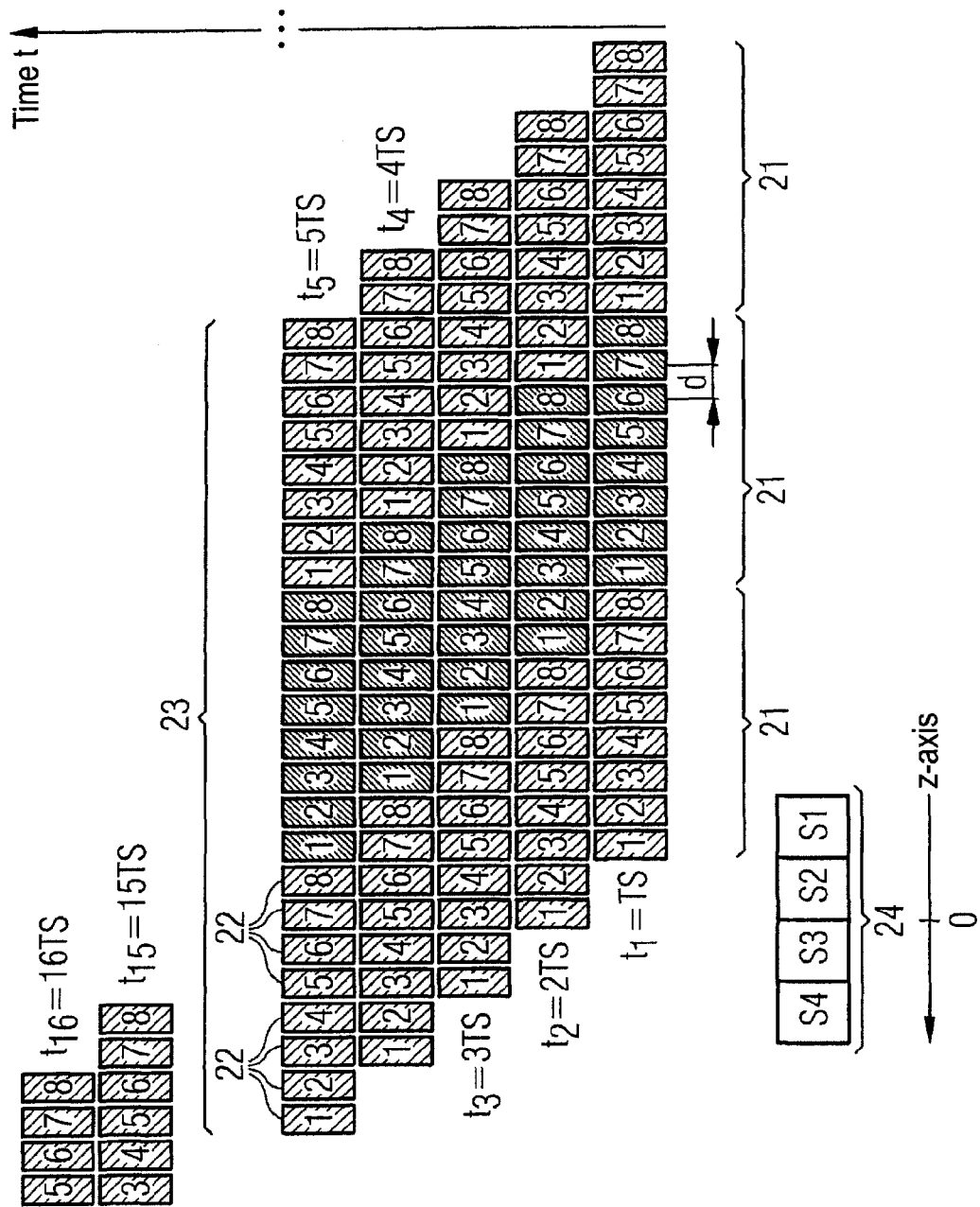

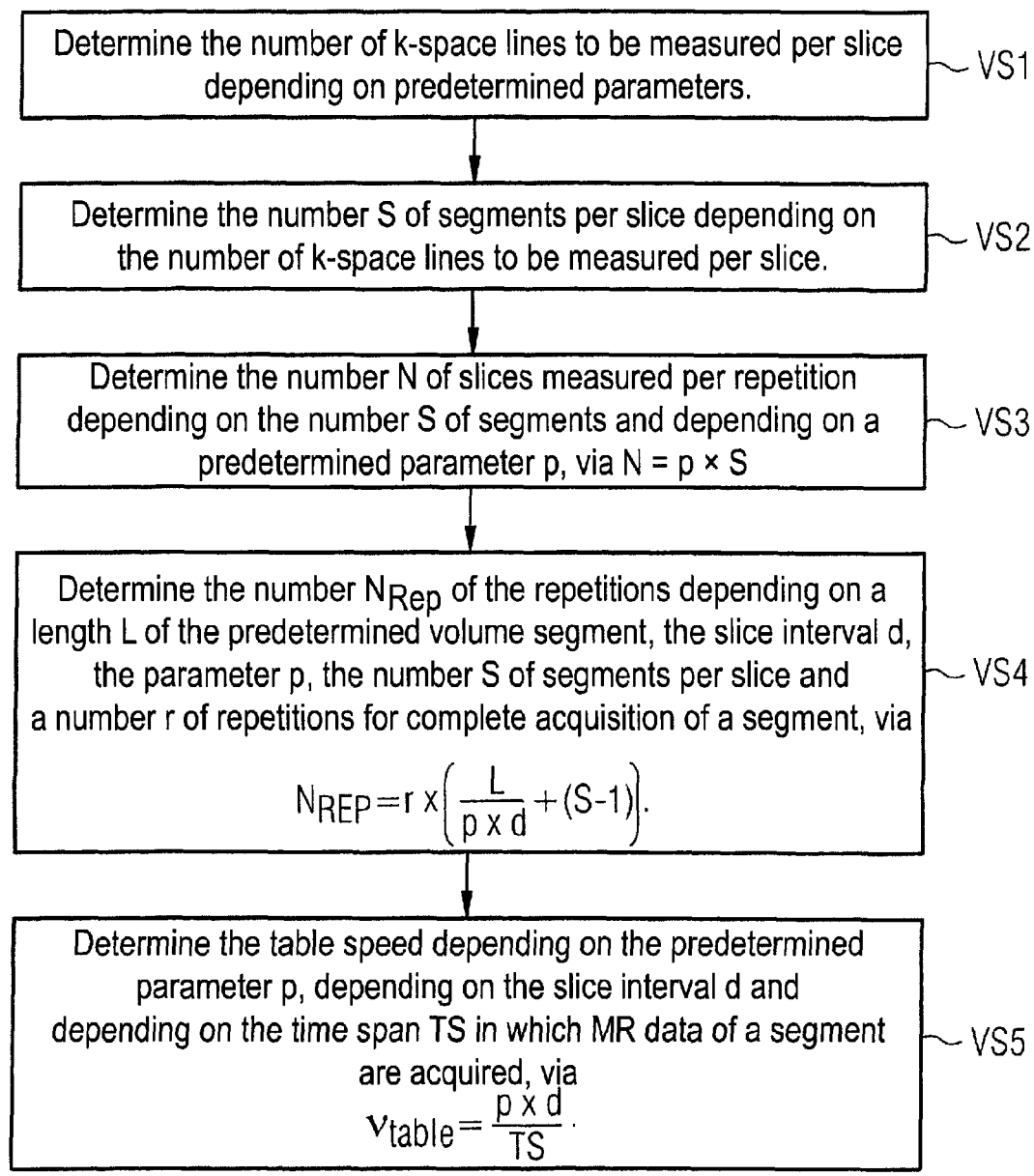

METHOD AND DEVICE FOR CONTROLLING ACQUISITION OF MAGNETIC RESONANCE DATA IN A MAGNETIC RESONANCE APPARATUS

BACKGROUND OF THE INVENTION

1. Field of the Invention

The present invention concerns a method and a device in order to control the workflow of an MR measurement (data acquisition), wherein multiple slices of a predetermined volume segment of an examination subject are excited and measured in each repetition of the MR measurement with continuous table feed, particularly in such a method and device wherein the MR signals are acquired with the SMS technique ("Sliding MultiSlice" technique).

2. Description of the Prior Art

The SMS technique is a special axial multislice measurement with continuous feed of a patient bed during an MR measurement. Measurements with table driven continuously through the magnets of the magnetic resonance system serve to expand the "field of view" (FOV) in the direction of the table displacement and can simultaneously limit the measurement area within the magnet. Concurrent with the continuous table feed is the acquisition of the expanded field of view in multiple stations given a stationary table. After all data of a station are acquired, the patient is moved with the patient bed to the next station and exposed to the measurement during the travel. Given axial multislice measurements with continuous table feed, the examination region or the volume within the patient from which images should be acquired is normally subdivided into multiple slice stacks. Given simple axial multislice measurements with continuous table feed, these slice stacks are acquired in succession. During the measurement of one of these slice stacks, the measurement position follows a fixed anatomical position within the examination subject driven with the table. The speed with which the table is continuously moved is selected such that the travel path during the acquisition time of a slice stack is, for example, equal to twice the length of a slice stack. It is thereby possible for corresponding slices of different slice stacks to be measured identically. Different slices of a slice stack or different slices of different slices stacks are measured differently, however. In particular, k-space lines of the slices that correspond to one another are measured (acquired) at different positions within the magnetic resonance system. This has the following disadvantage.

Since the B0 field of every real magnetic resonance system is not ideally homogeneous, and the gradient fields are not ideally linear, similar MR measurements at different positions lead to different distortions of the calculated images. After the composition of the images, this leads to discontinuities at the borders of the slice stacks since anatomically adjacent slices that are associated with different slice stacks occupy opposite positions within the respective slice stack. This problem is addressed and improved by the SMS technique, for example.

The SMS technique described by H.-P. Fautz and S. A. R. Kannengiesser in "Sliding Multislice (SMS): A New Technique for Minimum FOV Usage in Axial Continuously Moving Table Acquisitions", Magnetic Resonance in Medicine 55:363-370 (2006) allows acquisition-dependent differences between different slices of a slice stack to be minimized in comparison to other acquisition techniques. However, specific requirements with regard to the number of slices of a slice stack and with regard to the user parameters defining a resolution of the achieved imaging must be satisfied in specific MR measurements in which multiple slices are acquired with continuous table feed (for example in the SMS technique).

SUMMARY OF THE INVENTION

These requirements considerably hinder the preparation and the implementation of such an MR measurement. Therefore, it is an object of the present invention to simplify the preparation and the implementation of such an MR measurement in spite of the requirements to be satisfied.

In accordance with the present invention, in a method for controlling the workflow of an MR measurement in a magnetic resonance system. MR signals are acquired from a predetermined volume segment given continuous feed of the patient bed. The volume segment is subdivided into parallel slices with a constant slice interval, such that the direction of the table feed is perpendicular to the slice plane. Furthermore, data of N slices are normally respectively excited and read out during each repetition of an underlying basic sequence. The number of slices excited and read out per repetition of the underlying basic sequence is selected automatically depending in particular on the parameters defining the image contrast and the image resolution and cannot be directly preset by a user of the magnetic resonance system.

In a measurement according to the SMS technique, k-space of every slice is subdivided into S k-space segments, and the k-space data that are associated with a k-space segment are measured when the respective slice is located at a specific location within the active volume of the MR system.

A division of the active volume inside the magnetic resonance system therefore results, again into S sections. Because the same k-space data of different slices are measured at the same (or neighboring) positions within the magnetic resonance system, acquisition-dependent differences as a result of the nonlinearity of the gradient system or the inhomogeneity of the B0 field are avoided or reduced. However, an SMS measurement (as explained in more detail below) can be implemented only if specific correlations are satisfied between the number of segments, the table speed, the number of slices that are excited and read out per repetition of the underlying basic sequence, and additional parameters. These correlations are absent in a conventional measurement without continuous table feed and complicate the preparation of a SMS measurement significantly. These problems are avoided or reduced according to the invention because the number of slices that are measured per repetition of the underlying basic sequence cannot be predetermined by the user of the MR system (as in conventional measurements), but rather is determined automatically depending on parameters determining the workflow of the MR measurement (for example the number of k-space segments per slice, or for example parameters which affect an image contrast and/or an image resolution of the MR images created by the MR measurement).

As used herein, the term "basic sequence" means a specific series of radio-frequency pulses that are radiated into the examination subject and rapidly switched (activated) magnetic gradient fields that are superimposed on the basic magnetic field, as well as the detection of the signal emitted by the examination subject. The acquired measurement data are digitized and stored as complex numerical values in a k-space matrix. The k-space matrix can be divided into multiple segments S, as stated above. A characteristic radio-frequency pulse of the basic sequence is the excitation pulse that excites a nuclear magnetic resonance in the examination subject. In connection with the present invention, spatially selective excitation pulses are thereby used. A gradient field is thereby switched during a suitable radio-frequency pulse such that a nuclear magnetic resonance is triggered in the examination subject only in a partial volume that is limited in the direction of the gradient field. This partial volume is designated as a slice. In a repetition of the basic sequence, multiple different slices are excited and the emitted signal is respectively spatially coded (with the use of gradient fields) and detected, with only one excitation pulse activated per slice, however. At least one k-space line is acquired per repetition in all slices excited and measured per repetition. A repetition of the basic sequence occurs frequently until all slices within the predetermined volume segment (meaning all segments of each slice) have been completely acquired.

The visualization of the multiple slices that are excited and measured per repetition can be displayed to an operator in the form of a slice stack, i.e. as multiple slices stacked atop one another.

When the MR measurement is implemented with the SMS technique, for example, k-space of every slice can be subdivided into multiple k-space segments, wherein one or more k-space lines are acquired per repetition only in one segment of a slice.

The determination of the number of slices that are measured per repetition of the underlying basic sequence can be determined dependent on the number of k-space lines per slice, for example. For this purpose, the number of k-space lines is selected depending on the parameters determining the image resolution, which parameters are predetermined by (for example) an operator for the control of the workflow of the MR measurement. Depending on this number of k-space lines, one or more of the following parameters can then be derived:

the number of slices that are measured per repetition of the underlying basic sequence, the table speed with which the table on which the patient to be examined lies is slid continuously through the magnetic resonance system, the total number of repetitions of the underlying basic sequence until the data of all slices of the predetermined volume segment are measured.

For example, if a user parameter is changed so that the number of k-space lines to be measured is altered, the number of slices per repetition of the underlying basic sequence, the table speed and the total number of repetitions of the basic sequence are normally also re-determined.

In a preferred embodiment, the calculation of the number of k-space lines of each slice that are to be measured is subject to the boundary condition that this number should be an integer multiple of the number of k-space lines per segment. Therefore the number of k-space lines to be measured is determined as follows according to a preferred embodiment according to the invention.

First the number of the minimum k-space lines to be measured per slice is determined depending on the predetermined parameters affecting the workflow of the MR measurement (for example the resolution). The number of the minimum k-space lines to be measured per slice is the number of k-space lines of the respective slice that must be acquired at a minimum in order to achieve the resolution defined by the predetermined parameter. According to this embodiment, the number of k-space lines to be measured is a whole-number multiple of the number of k-space lines per segment and is greater than or at least equal to the number of the k-space lines that are to be measured at a minimum.

In a turbo spin echo sequence or EPI sequence, the number of k-space lines per segment can be defined by the echo train length. In sequences such as FLASH or TrueFISP, in which normally only one k-space line is read out per excitation, the number of k-space lines per segment can be predetermined by a user, for example.

In the normal case, the number of k-space lines to be measured is greater than the number of k-space lines to be measured at a minimum. According to the invention, more k-space lines are accordingly measured than is necessary due to the predetermined parameters. These additionally measured lines, whose number results from a difference between the number of k-space lines to be measured minus the number of k-space lines to be measured at a minimum, can be used as follows.

The line interval in k-space is reduced to the value $\Delta k$ according to the following equation:

$$\Delta k = \Delta \tilde{k} \times \frac{\tilde{N}_{PE}}{N_{PE}},$$

wherein $\Delta \tilde{k}$ is the line interval which results from the field of view set by the user in the phase coding direction (short: "Phase FOV") and the oversampling set by the user in the phase coding direction (short: "Phase Oversampling"), and wherein $\tilde{N}_{PE}$ is the number of the k-space lines to be measured at a minimum per slice and $N_{PE}$ is the number of k-space lines to be measured per slice. The distance from the outermost k-space lines to the k-space center is thereby not varied. In other words, the oversampling in the phase coding direction is implicitly increased relative to the value set by the user (via the predetermined parameters). The signal-to-noise ratio of the calculated images is thereby advantageously increased.

In an MR measurement with PPI ("Partial Parallel Imaging"), the measurement operates with multiple reception coils and normally with an undersampling along the phase coding direction. Aliasing artifacts as a consequence of the undersampling are avoided in that the unmeasured k-space lines are substituted approximately during the reconstruction using the k-space lines measured with multiple reception coils and the sensitivities of the individual coils. In a PPI measurement, the additional lines can now be used to measure more densely in the center of k-space (i.e. with additional k-space lines) so that no undersampling or at least a lesser undersampling occurs in the k-space center. In the event that the k-space center is already scanned without an undersampling in a special PPI technique, the additional lines can be used to correspondingly enlarge the region in the k-space center which is acquired without undersampling. These additional lines then do not need to be calculated in the image reconstruction (since they are measured), which in turn increases the signal-to-noise ratio. If the more densely scanned region in the k-space center is additionally used to calculate the coil sensitivities, a larger region can moreover additionally stabilize the PPI reconstruction.

The additional lines, moreover can be used in order to measure a few lines of k-space repeatedly. These repetitions can either not be read out or be discarded during the reconstruction, or be used for averaging the signal to be acquired, wherein the signal-to-noise ratio is advantageously increased via the latter.

Starting from the number $N_{PE}$ of the k-space lines to be measured per slice (which has been determined in advance), the number S of segments per slice can be determined depending on the number A of k-space lines per segment by means of the following Equation (1):

$$S = \frac{N_{PE}}{A} \quad (1)$$

The number A of k-space lines per segment can in turn be determined by an echo train length or be set equal to a predetermined value.

As is explained in further detail in the following, the expansion of the active volume in the direction of the table feed (thus the range which a slice travels during its data acquisition in the magnetic resonance system) is linked with the number of segments in the SMS technique. The larger this region, the greater the deviations with regard to the $B_0$ homogeneity or, respectively, with regard to the gradient linearity in this region, and the greater the image distortions or artifacts as a result of the data acquisition at varying positions within the magnetic resonance system. Therefore, the number of segments per slice should not be too large, nor the number of k-space lines per segment too small.

In the event that the number of k-space lines per segment is predetermined by the user by means of a new parameter, this new parameter allows the user to choose between a high table speed and therefore short measurements (given a small value of the new parameter) and/or a small number of slices (and therefore a small extent of the active volume in the direction of the table feed) and therefore low-distortion/artifact images (given greater values of the new parameter).

According to the invention, alternative determinations of the number of segments are also conceivable, for example in sequences in which only one k-space line is read out per excitation (echo train length 1). In particular a measurement time per slice (i.e. until the MR data of the slice have been completely acquired) or a table speed could be predetermined. The number of segments could then be determined via Equation (1) cited above and Equations (2) and (4) which are disclosed in the following, such that the predetermined measurement time per slice or the predetermined table speed is realized.

After the number S of the segments has been determined, for example by means of one of the procedures described in the preceding, the number N of slices excited and read out per repetition of the underlying basic sequence can be determined depending on a factor p (that is to be provided) by the following Equation (2):

$$N = p \times S \quad (2)$$

The following is to be taken into account in the selection of the factor.

In multislice measurements, N slice excitations are implemented per TR interval (time span between two successive repetitions of a sequence). In particular spatially adjacent slices are thereby not excited in immediate succession. Rather, in a first pass through the slice stack (during the first half of the TR interval) every second slice (for example the slices with an even slice index) is initially excited. In a second pass which follows the first pass, the slices which were left out in the first pass (the slices with an odd slice index) are then excited during the second half of the TR time interval. The reason for this is the imperfect excitation profile of real radio-frequency pulses. Every radio-frequency pulse also affects regions which are located outside of the slice to be excited by the radio-frequency pulse; this is technically unavoidable. This effect (known as the "Cross Talk" effect) occurs primarily between directly adjacent slices. Due to the interleaved excitation schematic that was just described, at the point in time of the excitation of a specific slice its implicit and unwanted excitation due to the excitation of its neighboring slice has advantageously at least partially decayed.

As explained below in detail using FIG. 2, an SMS measurement with interleaved excitation scheme can be advantageously realized if the parameter p>1 is selected. However, there are special applications in which adjacent slices are excited in immediate succession. According to the invention it can therefore be predetermined whether directly adjacent slices should be excited in immediate succession or not. The parameter or factor p is thereby set equal to 1 if adjacent slices should be excited in immediate succession. In contrast to this, if an interleaved slice excitation order is predetermined, the factor p is set equal to 2. The number of slices that are excited and read out per repetition of the underlying basic sequence can be set via Equation (2) described above with this establishment of the factor p and with the determination of the number of segments according to Equation (1).

However, in other embodiments according to the invention it is also conceivable to implement an interleaved excitation order of the parameter p>2 is chosen. For example, if the user chooses the parameter p=3, a uniform sequence workflow (explained in detail in the following) is achieved in that an excitation order with three passes through the N slices in the active volume of the MR system is chosen. In the first pass (during the first third of the TR interval), every third slice is excited (for example the slices with the indices 1, 4, 7, ...). In the second pass (during the second third of the TR interval) the slices with the indices 2, 5, 8, ... are excited, and in the last pass (during the last third of the TR interval) the remaining slices with the indices 3, 6, 9, ... are excited. Accordingly, given arbitrary values of p (for example p>3) an excitation scheme with p passes through the N slices in the active volume of the MR system can be selected, wherein every p-th slice is excited in each pass. The parameter p thus allows the user to choose between a high table speed (and therefore short measurements; large values of p) and a small number of slices, and therefore low-distortion/artifact images (smaller values of p).

In a preferred embodiment, a start position of the bed is chosen such that the first slice of the predetermined volume segment enters into the active volume of the MR system precisely when, after an acceleration phase, the bed has reached the table speed calculated with the Equation (4) presented below. This point in time then also defines the start of the MR measurement. The MR measurement is ended as soon as the last slice within the predetermined volume segment leaves the active field of view in the center of the magnetic resonance system, thus as soon as the predetermined volume segment has been completely acquired or detected. At the beginning and at the end of the MR measurement, slices are therefore located in the active volume of the MR system that adjoin the predetermined volume segment and whose data are not completely acquired. To reduce the SAR load (SAR="Specific Exposure Rate") of the patient, the excitation of these slices can be suppressed. Due to the "cross talk" effect describe above, however, this would change the contrast and the intensity of the border slices of the predetermined volume segment. Therefore, it is more advantageous to nevertheless excite the slices that lie outside the predetermined volume segment but to not read out the data or, respectively, to discard the readout data.

With the start point in time and end of the MR measurement that were just described, the travel path of the bed during the MR measurement exceeds the length of the predetermined volume segment in the direction of the bed feed by approximately the extent of the active volume in the direction of the bed feed. The total number $N_{REP}$ of repetitions of the basic sequence can be calculated from this travel path and the bed feed per repetition of the underlying basic sequence (or, respectively, the bed speed and the duration of a repetition):

$$N_{REP} = \frac{L+(S-1)\times p \times d}{p \times d/r}$$
$$= r \times \frac{L+(S-1)\times p \times d}{p \times d}$$
$$= r \times \left(\frac{L}{p \times d} + (S-1)\right) \quad (3)$$

r is the number of repetitions of the underlying basic sequence that is necessary for the measurement of a k-space segment. L is the length of the predetermined volume segment in the direction of the travel path of the table or of the bed, and d is the slice interval.

According to the invention, the determination of the predetermined volume segment can ensue graphically using images of a localizer, as is known from other techniques with or without continuous table feed. It is also possible according to the invention for the predetermined volume segment to be predetermined indirectly by the total number of slices to be measured and by the slice interval. The specification of the total number of slices to be measured can ensue either numerically or graphically. Given the graphical specification of the total number of slices to be measured, this can be conducted by (for example) "raising" or "pushing together" a virtual slice stack which visualizes all slices to be measured.

A localizer is a known tool with which the inside of a body can be observed and a specific region or a specific volume there can be defined. These are normally overview images that are acquired with a fast MR sequence at the beginning of the MR examination of the patient but that are not suitable for diagnosis due to their low resolution or their contrast.

Depending on the parameter p, the slice interval d and the time interval TS at which the MR data of a segment are acquired, the table speed $v_{table}$ can be determined via the following equation $$v_{table} = \frac{p \times d}{TS}. \quad (4)$$

The time interval TS is equal to the product of A×TR, wherein TR is defined here as the time that passes during a repetition of the underlying basic sequence.

The length of the predetermined volume segment in the direction of the table feed is advantageously limited to values that are an integer multiple of the slice interval d. The length of the active volume in the direction of the table feed is implicitly determined by the number of slices N that are excited and read out per repetition of the underlying basic sequence and the slice interval d, and is equal to N×d.

In particular the following boundary conditions should be adhered to in the determination of the parameters to control a workflow of an MR measurement:

The specific number of slices that are excited and read out per repetition of the underlying basic sequence should not be greater than a number of slices which can be excited, coded and read out in a TR interval.

The determined table speed should not be greater than the maximum specific table speed.

The determined length of the active volume in the center of the magnetic resonance system should be defined in the direction of the travel path of the table such that the active volume lies within a specified volume inside the magnetic resonance system in which a specified magnetic field homogeneity and a specified gradient linearity are achieved.

The limit conditions described above show that the parameters determining the workflow of the MR measurement can be limited and set depending only on one another in order to generate a consistent measurement protocol (i.e. a parameter set) by means of which an MR measurement can be implemented by the SMS technique.

For example, if the inventive determination of the number of slices N that are excited and read out per repetition of the underlying basic sequence delivers a value that is too large relative to the TR value (normally) provided by the user, an implicit adaptation of the TR interval is not a viable path since the contrast of the generated images is normally also altered by a variation of the TR interval. In other words, the TR interval cannot be varied; rather, instead other parameters (for example the parameter p or the number S of segments per slice) must be adapted such that the number of slices to be excited and measured per repetition is in a range which can be excited, coded and read out in a TR interval.

In accordance with the present invention, this problem is addressed by a limitation of the value ranges of the parameters affecting the workflow of the MR measurement. For example, this means that the value range of the parameters that is provided to a user contains only those values that lead to a number of slices that can be excited and measured per repetition of the underlying basic sequence. This means that the value range of the parameters from which a user can select a value for the corresponding parameters generally differs in the present invention from the value range of the parameters of a corresponding protocol of a conventional measurement in that values that could be set in a conventional measurement do not belong to the value range of the corresponding parameters that is provided to the user according to the invention.

The generation of the value ranges of the corresponding parameters that are provided to the user thereby ensues as follows according to the invention:

Values are iteratively selected from a value range specified for every parameter—which value range is normally greater than the value range that is ultimately provided to the user—and is respectively set as a value for the corresponding parameter. With the aid of a check routine it is subsequently checked whether the corresponding variation of the parameter leads to a measurement-capable protocol. Only if this is the case is the respective parameter value also a component of the value range for the corresponding parameter that is provided to the user.

This procedure to generate value ranges provided to the user is known from the U.S. Pat. No. 7,051,286, for example.

It is noted that, due to the variation of one parameter, normally the value ranges provided to the user for additional parameters must be accordingly varied according to the invention so that they have only those values for the corresponding parameters which, together with the newly varied parameter, lead to a measurement-capable protocol.

The present invention also encompasses a device for a magnetic resonance system to control a workflow of an MR measurement. The device has a control unit in order to control (operate) the magnetic resonance system; a receiver device in order to receive MR data that are acquired by the magnetic resonance system; and an evaluation device in order to evaluate the received MR data. The device is designed such that the device controls the magnetic resonance system through the control unit such that the magnetic resonance system detects MR signals from a predetermined volume segment, in particular by means of the SMS technique. The magnetic resonance system thereby excites multiple slices of the predetermined volume segment per repetition given a continuous table feed and measures these slices. The device thereby automatically determines the number of slices which are excited and measured per repetition depending on parameters determining the workflow of the MR measurement, i.e. the number of slices which can be excited and measured per repetition cannot be directly predetermined by a user via a parameter.

The advantages of the device according to the invention essentially correspond to the advantages of the method according to the invention that have been described above.

Furthermore, the present invention discloses a magnetic resonance system that has a device according to the invention.

Moreover, the present invention describes a computer program product (in particular a software) which can be loaded into a memory of a programmable controller or, respectively, a computer of a magnetic resonance system. All or various embodiments of the method according to the invention that are described in the preceding can be executed with this computer program product when the computer program product runs in the controller. The computer program product thereby possibly requires program means (for example libraries and auxiliary functions) in order to realize the corresponding embodiments of the method. In other words, in particular a software with which one of the embodiments of the method according to the invention that are described above can be executed should be protected with the Claim directed towards the computer program product.

The present invention also encompasses an electronically readable, non-transitory data medium (for example a DVD), a magnetic tape or a USB stick encoded with electronically readable control information, in particular software. When this control information (software) is read from the data medium and stored in a controller or computer of a magnetic resonance system, all embodiments according to the invention of the method described in the preceding can be implemented. The software can thereby be a source code (for example in C++) that must still be compiled and linked or must only be interpreted, or an executable software code that is merely to be loaded into the corresponding computer for execution.

For example, with the present invention an SMS measurement can be operated largely like a conventional measurement (from the user point of view) in which the table is not moved during the measurement. From the user point of view, the significant difference between the present invention and conventional methods and devices to control an MR measurement is that the examination region (the predetermined volume segment) in the direction of the table feed is established not by the number of slices of a slice stack but rather by a new parameter. If this establishment ensues by a graphical placement of the predetermined volume segment by means of a localizer, this establishment is intuitive and known to at least some users from other measurement techniques with continuous table feed. The alternative establishment by "raising" or "pushing together" a virtual slice stack which covers the examination region is likewise intuitive. The total number of slices that is hereby established by the user is thereby completely uncoupled from the slices to be measured per repetition of the underlying basic sequence. This facilitates the preparation even in comparison to the preparation of a conventional MR measurement since the examination region can be selected perpendicular to the slice plane, independent of TR.

With the present invention, the user does not have to be responsible for correlations between parameters that are specific to the employed technique with continuous table feed (for example the SMS technique). Therefore, these dependencies do not need to be known to the user since, given every alternation of a parameter, the parameters dependent on this (for example the number of k-space lines to be measured, the number of segments, the number of slices excited and read out per repetition of the basic sequence, the table speed, the total number of repetitions of the underlying basic sequence) are set such that the SMS requirements for a consistent protocol are satisfied. This advantageously reduces the amount of training for the operator.

In comparison to methods according to the prior art, apart from establishing the predetermined volume segment in the direction of the table feed, the present invention requires no additional, unfamiliar (i.e. new) user specifications. For example, an interleaved slice excitation order can thus be realized by an implicit setting of the parameter p so that no direct setting of the parameter p is necessary.

Moreover, the present invention offers advantages in the setting of the parameters for an SMS measurement (for example in the adaptation of the predetermined volume segment in the phase coding direction to the individual dimensions of the patient to be examined, which normally affect the minimum k-space lines to be measured) for a user trained in the SMS technique since, according to the invention, the SMS requirements for a consistent protocol are automatically taken into account so that, even for a trained user, the measurement preparation (and therefore the entire examination workflow) is advantageously shortened.

According to the invention, starting from a protocol appropriate for the examination task, a user can only vary the parameters such that a measurement-protocol or a consistent protocol exists again after this variation. By contrast, a method or a magnetic resonance system that operates without the present invention would need to have, at the start of the measurement, a way to handle an inconsistent protocol in which the SMS requirements are not satisfied. For example, this could be a termination of the start of the SMS measurement or—as is typical according to the prior art—to implement the measurement without the SMS technique. The first variant is clearly not a good solution since neither is the user given assistance to achieve a consistent protocol, nor is an MR measurement implemented. However, the second variant is also not a good solution since, for the average user, it would lead to quality fluctuations of the generated MR images (dependent on whether the SMS technique can be used or not) that are difficult to understand.

The present invention is in particular suitable to control a workflow of an MR measurement in a magnetic resonance system by means of the SMS technique. Naturally, however, the present invention is not limited to this preferred application field since the present invention can also be used merely to generate a parameter set or a protocol for an MR measurement without the MR measurement actually being implemented.

BRIEF DESCRIPTION OF THE DRAWINGS

A magnetic resonance system according to the invention with a control device according to the invention is schematically shown in FIG. 1.

The implementation of an SMS measurement according to the invention over time is shown in FIG. 2.

A method according to the invention to determine parameters for an MR measurement by means of the SMS technique is shown in FIG. 3.

DESCRIPTION OF THE PREFERRED EMBODIMENTS

Figure 1:
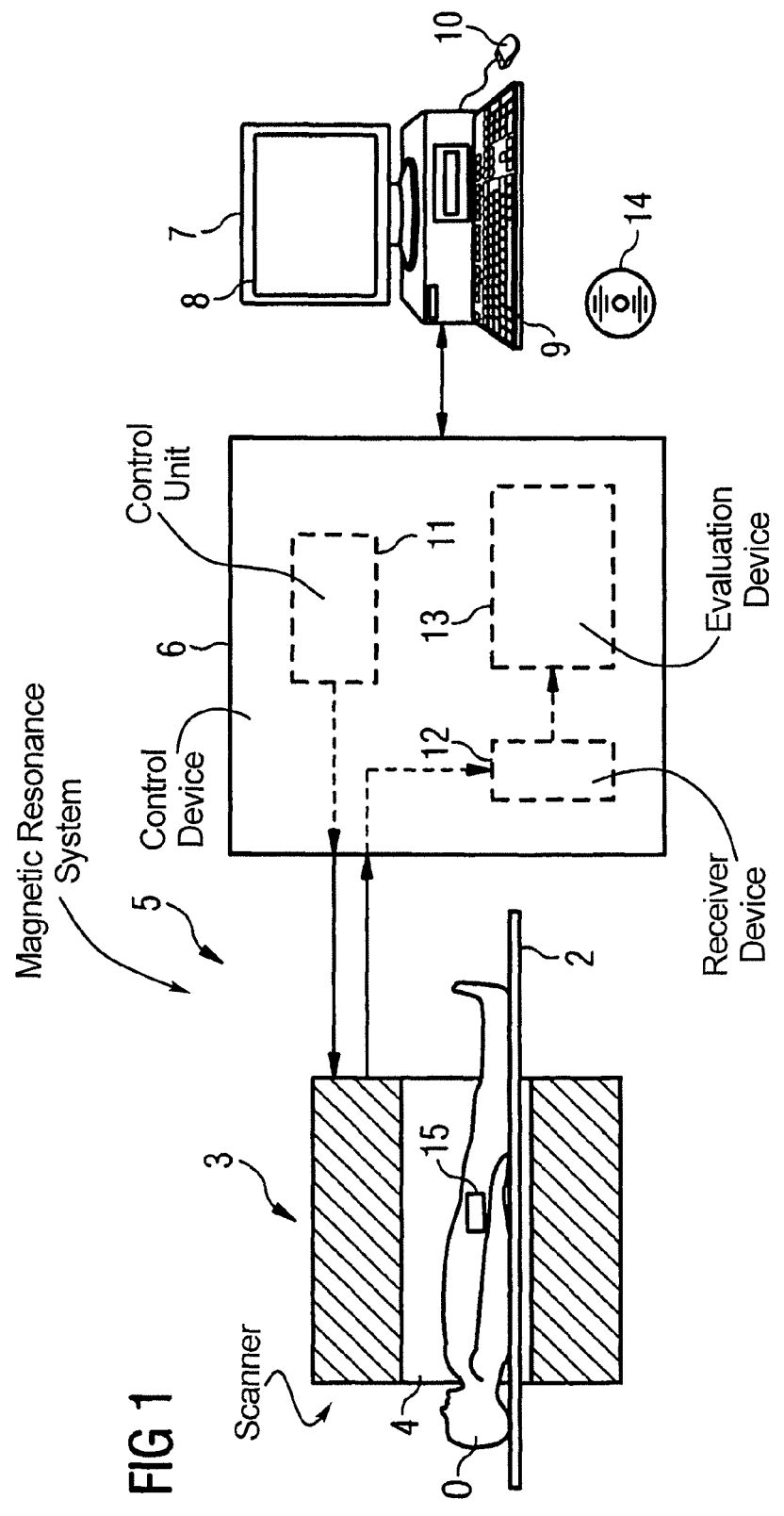

A magnetic resonance system 5 according to the invention is schematically shown in FIG. 1. The magnetic resonance system 5 has a scanner 3 (data acquisition unit) with which the magnetic fields necessary for the MR examination are generated in a measurement space 4, The system 5 also has a table 2, a control device 6 with which the scanner 3 is operated and MR data are acquired by the scanner 3, and a terminal 7 connected to the control device 6.

The control device 6 includes a control (operating) unit 11, a receiver device 12 and an evaluation device 13. During an MR examination, MR data are received by the receiver device 12 by the scanner 3, with the scanner 3 and the table 2 being controlled by the control unit 11 such that MR data are acquired in a measurement volume 15 that is located inside the body of a patient O lying on the table 2.

The evaluation device 13 then prepares the MR data such that they can be graphically presented on a monitor 8 of the terminal 7 and such that images generated according to the invention are displayed. In addition to the graphical representation of the MR data, a volume segment to be measured (for example) can be provided by a user and additional parameters for implementation of the method according to the invention can be determined with the terminal 7 (which comprises a keyboard 9 and a mouse 10 in addition to the monitor 8). The software for the control device 6 can also be loaded into the control device 6 (in particular into the evaluation device 13) via the terminal 7. This software for the control device 6 can thereby also comprise the method according to the invention. It is thereby also possible that the method according to the invention is contained in a software which runs in the terminal 7. Independent of in which software the method according to the invention is contained, the software can be stored on a DVD 14 so that this software can then be read by the terminal 7 from the DVD 14 and be copied either to the control device 6 or to a computer of the terminal 7 itself.

An implementation of an SMS measurement according to the invention is shown in FIG. 2. The horizontal z-axis points in the direction of the table feed, i.e. in the direction in which the table 2 shown in FIG. 1 is continuously displaced during the implementation of the SMS measurement. The shown zero point of the z-axis is located at the isocenter of the magnet or, respectively, the scanner 3 (see FIG. 1). Time is shown on the vertical axis. The respective eight slices 22 to be measured per slice stack 21 are represented with the characters 1 through 8 corresponding to their order in which they enter into the center of the scanner 3 in the direction of the table feed into the active volume 24. As many slices as are excited and read out per repetition of the underlying basic sequence are thereby associated with each slice stack. The extent of a slice stack in the direction of the table feed is therefore equal to the extent of the active volume 24 in the direction of the table feed. The extent of the active volume 24 in the direction of the table feed is designated as active field of view or, respectively, active FOV in the following. The predetermined volume segment 23 to be examined or examination region is subdivided into three slice stacks 21 of eight slices 22 each in the direction of the table feed.

K-space of every slice 22 is subdivided into four respective segments. It therefore results according to Equation (2) described above that the factor p=2. Each of these four segments is associated with one of the four sections S1-S4 of the active volume. A specific segment S1-S4 of a slice 22 is measured as long as the corresponding slice 22 is located in the section S1-S4 of the active field of view 24 that is associated with the segment. Corresponding segments of different slices 22 are accordingly measured at the same (or in the case of p>1, at least at an adjacent) position in the coordinate system of the scanner 3.

The first two slices 22 of the first slice stack 21 are presently located entirely in the first section 51 of the active field of view 24 at the point in time $t_1$. One time interval TS later, at the point in time $t_2$, these two slices 22 are located in the second section S2 of the active field of view 24, and the third and fourth slice 22 of the first slice stack 21 have entered into the first section S1 of the active field of view 24. The table speed (table feed per time interval TS) accordingly satisfies the corresponding SMS requirements and amounts to p or, respectively, 2 slice intervals d per time interval TS. At the last point in time $t_{16}$ shown in FIG. 2, the last two slices 22 of the third and last slice stack 21 have just left the last section S4 of the active field of view, such that the measurement is ended.

Since each slice 22 passes through the sections S1 through S4 to acquire its MR data, the position of the respective slice 22 is different in the different measurements of its segments. The examination region of an SMS measurement with continuous table feed is therefore normally greater than the region that is covered by the slice stack 21. The parameter number N of the slices 22 per slice stack 21 therefore loses some of its importance, for example in comparison to a conventional multislice measurement with standing table 2.

The following characteristic with regard to the SMS technique should be noted using FIG. 2, wherein a slice 22 is considered which moves through the active volume 24 during the SMS measurement. Its first excitation and MR data acquisition thereby ensues at the point in time $t_0$ at the location $z_0$ relative to the z-axis in FIG. 2. After the complete acquisition of the first segment at the point in time $t_1=t_0+TS$, the slice has traveled p slice intervals d or, respectively, the distance p×d and is located at the location $z_1=z_0\pm p\times d$, wherein the plus or, respectively, minus sign is to be chosen depending on the respectively chosen direction of the table feed. If p=2 now, as is the case in the example shown in FIG. 2, and the slice excitation order travels interleaved with two passes through the slice stack 21, the slice 22 is located at exactly the location at which that slice 22 that was excited immediately after or, before it at the point in time $t_0$.

If the time interval between two immediately successive excitations $\Delta t=TR/N$, the temporally second excitation ensues at the point in time $t=t0+\Delta t$ at the location $z=z0\pm 2\times d\pm v_{table}\times\Delta t$. The summand "2×d" essentially states that the second excitation occurs two slice intervals away from the first excitation, wherein what is considered via the summand "$v_{table}\times\Delta t$" is the movement of the table 2 between the first and second excitation. The plus or, respectively, minus sign before the summand "2×d" takes into account whether the second excitation in FIG. 2 occurs in the direction of the z-axis or counter to the direction of the z-axis relative to the first excitation, while the plus or, respectively, minus sign before the summand "$v_{table}\times\Delta t$" takes into account the direction of the table feed.

For the special case p=2 (that is also shown in FIG. 2) and an interleaved slice excitation with two passes through the slice stack 21, the sequence workflow can be repeated identically after r×TR intervals insofar as a small deviation is accepted between the physical $TR_{physical}$ interval and the repetition time TR of the sequence. The physical TR interval is the time span between two immediately successive excitations of the same slice and, for example, amounts to $TR_{physical}=TR\pm\Delta t=TR\times(1\pm 1/N)$ for an echo train sequence (r=1). For sequences in which one k-space line is measured per excitation, r is therefore equal to A (r=A), where A is the number of k-space lines per segment. Given echo train sequences, a complete segment (thus A k-space lines) is normally read out after every excitation, and r is therefore equal to one (r=1).

According to experience, a particularly more uniform sequence workflow has a positive effect on transient phenomena and eddy current curves, and therefore on the image quality an the noise level generated by the magnetic resonance system 5 during an MR measurement. Therefore the interleaved slice excitation order described above is preferable for the case p=2.

In order to avoid misunderstandings in the nomenclature: what is to be understood by a repetition of the underlying basic sequence is the successive excitation of N different slices and normally the readout of the generated MR signals following the respective excitation. The duration of a repetition of the underlying basic sequence is designated with TR. In the preferred embodiment just described with N=p×S and with interleaved excitation order with p passes through the N slices for p>1 or, respectively, non-interleaved excitation and p=1, the following applies. If the underlying basic sequence is an echo train sequence in which A lines are acquired per echo train, TS is thus equal to TR and the sequence is repeated identically in the reference system of the MR system after each TR interval (also with regard to the location of the excitation). In contrary to this, if the basic sequence is a sequence in which only one k-space line is read out per excitation, r=A, TS=r×TR=A×TR. In these sequences the location of the excitation differs in the reference system of the MR system in successive repetitions (at least in an optimal embodiment) during the acquisition of a segment such that the location of the excitation in the examination subject does not change. In the reference system of the MR system, the sequence is thus repeated absolutely identically only every r TR intervals (thus after TS).

In the following a characteristic of the SMS measurement that was already described further above, that the underlying basic sequence must be taken into account in the calculation of the total repetitions, is explained using FIG. 2.

In the SMS technique, the first and last repetitions (in particular the first repetition and last repetition) are less effective than the intervening repetitions. For example, if the first time interval TS in FIG. 2 is considered, p slices 22 arrive in the first section S1 of the active volume 24 of the scanner 3 in this time interval TS, and the k-space segment which is associated with this first section S1 is measured for these p slices 22. However, also located in this time interval are (N−p) additional slices that lie outside of the predetermined volume 23 and could be measured in the active volume 24 of the scanner 3 and the corresponding segments. However, these (N−p) slices 22 leave the active volume 24 before all S segments of these slices 22 can be measured, since in particular the k-space segment which is associated with the first section S1 cannot be measured for any of these (N−p) slices. Nevertheless, it would also be possible to acquire data for these (N−p) slices 22 and to calculate images from these. However, due to the absent or unacquired k-space segments (depending on the measurement technique) these images would have either artifacts or at least a lower resolution than is predetermined by the user through parameters. For example, the latter runs the risk that smaller lesions are overlooked. Therefore the data for the (N−p) slices 22 that occupy positions within the active volume 24 during the first time interval TS but which lie outside the predetermined volume 23 are either not acquired in the first place or are discarded during the image reconstruction procedure.

The same applies for those slices which enter into the active volume 24 after the last p slices 22 of the last slice stack 21 have left the first section S1.

In a preferred embodiment according to the invention, the user specifies only the predetermined volume segment 23, thus only the region from which images are calculated. From this the start position and end position of the bed are implicitly, automatically calculated, which is largely transparent for the user. The acceleration phase of the bed that is traversed before the bed has reached constant speed is advantageously also taken into account in this calculation. Therefore the user advantageously does not need to care about the difference between the traversed examination region and the region (predetermined volume segment 23) from which images are calculated, such that this deviation does not necessarily need to be known to the user.

A method according to the invention for the determination of a consistent parameter set or protocol is shown in FIG. 3.

In the first method step VS1, the k-space lines to be measured per slice are determined depending on predetermined parameters via which, for example, the resolution of the images to be generated is preset.

Depending on the k-space lines to be measured that are determined in the first method step VS1, the number S of the k-space segments per slice is subsequently determined in the second method step VS2, wherein this number S of the segments or their calculation can be dependent on additional preset parameters, for example an echo train length, a number of lines per segment, table speed, etc.

In order to determine the number of slices per repetition of the underlying basic sequence via the now-known number of segments, a value for the parameter p is still required for the third method step VS3 in order to then calculate the number of slices per repetition of the underlying basic sequence via the relationship specified in Equation (2).

The slices of the predetermined volume segment are thereby divided up into p groups according to a specific pattern to implement the MR measurement according to the SMS technique. If p=2, slices with even slice index are associated with the first group, for example, and slices with odd slice index are associated with the second group. A division of the slices into three (or generally p) groups ensues analogously, meaning that every third or, respectively, p-th slice is respectively associated with a group corresponding to p.

Moreover, what is known as an active volume 24 is selected in the center of the scanner 3 such that it exhibits the same extent of N slice intervals in the direction of the table feed. This active volume 24 is subdivided along the z-axis (see FIG. 2) into N/p sections S1-S4 of equal size. The number of sections S1-S4 is therefore equal to the number S of segments, wherein the extent of every section S1-S4 in the direction of the z-axis corresponds to the product of the parameter p and the slice interval d. Every segment is associated with a section S1-S4 of the active field of view, meaning that the same segment of the respective slice located in the respective section S1-S4 is always measured in every section S1-S4. In this association, those segments which contain k-space lines that lie in the neighborhood of the k-space center are advantageously associated with sections that exhibit an optimally small distance on the z-axis from the isocenter of the scanner 3 (zero point on the z-axis).

In a fourth method step VS4, the total number of repetitions of the underlying basic sequence is determined depending on the length of the predetermined volume segment in the direction of the table feed L, the slice interval d, the number of segments determined in step VS2, the predetermined parameter p, and the sequence-dependent number of the repetitions r per k-space segment, using Equation (3) described in the preceding.

In the fifth method step VS5 the table speed s calculated depending on the parameter p required for the third method step VS3, the slice interval d already required in the fourth method step VS4, and depending on the time interval TS=r× TR in which the MR data for a k-space segment of a respective slice are acquired, according to Equation (4) stated in the preceding.

The time interval TS corresponds to the product of a factor r and the time interval TR. The time interval TR is thereby the repetition time of the underlying basic sequence, thus the time between two repetitions. The factor r is a positive whole number which depends on the selected sequence type and specifies the number of repetitions of the underlying basic sequence that is necessary to measure a k-space segment. In echo train sequences—for example TSE sequences (TSE="Turbo Spin Echo") or EPI sequences (EPI="Echo Planar Imaging")—a complete segment is normally read out after a single excitation pulse so that r=1. Given gradient echo sequences (for example FLASH=Fast Low Angle SHot" or TrueFISP ("True Fast Imaging with Steady state Precession") only one line is read out per excitation pulse, and thus r is equal to the number A of k-space lines per segment. It is important that the time interval TR is long enough that all N slices can be excited, coded and read out during the TR time interval.

A decisive requirement for implementation of the SMS technique is thereby that the table 2 is moved by precisely p slice intervals d in the direction of or counter to the direction of the z-axis during the acquisition time TS of a segment. In other words, equation (4) is satisfied.

Under the requirement that the method according to the invention that is shown in FIG. 3 has been implemented successfully, and thus all requirements for a consistent parameter set for an SMS measurement are satisfied, the implementation of the SMS measurement should be explained again from a different viewing angle with reference to FIG. 2.

For this the first slice stack 21 (the slice stack to the left in FIG. 2) which enters first into the active field of view 24 of the scanner 3 (in the section S1) at the beginning of the SMS measurement is initially considered. Due to the conditions of Equations (2) and (4), precisely p slices (accordingly two slices 22 in the example of FIG. 2) enter into the first section S1 of the active volume 24 of the scanner 3 during a first time interval of the duration TS. During the first time interval TS the k-space segment which is associated with the first section S1 of the active field of view 24 is measured. In the second time interval TS, these p slices enter into the second section S2 of the active field of view 24, and the k-space segment which is associated with the second section S2 of the active field of view 24 are acquired for the p slices. During the same second time interval TS, the next p slices 22 of the first slice stack (with slice index p+1, . . . , 2p) enter into the first section S1 of the active field of view 24. For these p slices, the k-space segment which is associated with the first section S1 is acquired during the second time interval TS. This workflow is correspondingly continued.

After S (number of segments) time intervals of the duration TS, i.e. after four time intervals TS in the example of FIG. 2, the last p slices 22 of the first slice stack 21 (with slice index N−p, . . . , N) have entered into the first section S1 of the active volume 24 and the data of the first p slices 22 have been completely acquired. During the next time interval TS, the first p slices 22 of the first slice stack 21 leave the active field of view 24, and the first p slices of the second slice stack 21 enter into the first section S1 of the active field of view 24.

It is noted that data of N slices 22 in total are acquired per repetition time TR as of the S-th time interval TS.

As has already been stated above, the requirements described above and expressed by Equations (2) and (4) significantly hinder the measurement preparation for an SMS measurement. The pulse sequences which are used in an MR measurement and the image calculation that is thereby implemented can be controlled by numerous parameters to be provided by the user. For example, parameters are available to the user with which he selects the anatomy to be examined (for example the number, the position, the alignment of the slices), with which he affects the contrast between the relevant tissues (for example T1/T2 contrast over the repetition time TR, the echo time TE, presaturation pulses for fat saturation), or with which he chooses the resolution depending on the size of the sought lesion (for example matrix, extent of the field of view, slice thickness), etc.

A measurement protocol (or abbreviated as a protocol or parameter set) assigns a value to each of these parameters and therefore describes a measurement job. A portion of these parameters is normally modified only be experts for optimization for a specific examination (image quality, measurement duration, guidelines) and stored as a protocol in the memory of the magnetic resonance system 5. These protocols are then used by the operator of the magnetic resonance system 5 (in Germany this is most often medical technical assistants (MTAs)) in the corresponding examinations. However, before the measurement some parameters are normally individually adapted by the operator to the patient to be examined. For example, this is necessary in order to adapt the protocol to the individual dimensions (to the size) of the patient or to the duration in which the respective patient can lie still and/or hold his breath. Additional individual adaptations can be necessary in order to prevent an overheating of the patient during the MR measurement.

However, the parameters of the pulse sequence can normally not be chosen independent of one another. Numerous dependencies exist between the parameters (for example between the time interval TR and the number N of slices that can be excited, coded and read out during one repletion of the basic sequence), of which only the most important are known to the trained and/or experienced operator. In an SMS measurement there now exist additional dependencies which are expressed by Equations (2) and (4). In preferred embodiments according to the invention, of the parameters contained by Equations (2) and (4) only the repetition time TR and the slice interval d are accessible directly (i.e. via the user interface).

The user can affect the number of k-space lines to be measured with a plurality of other parameters. For example, this occurs through the parameters "Phase FOV", "Phase Resolution", "Base Resolution", (Matrix), "Phase Oversampling", "Phase Partial Fourier", "Parallel Imaging Factor" and "Parallel Imaging Reference Lines".

The number S of segments normally also changes with the number of k-space lines to be measured. For example, in a turbo spin echo sequence the number $N_{PE}$ of the k-space lines to be measured and the number S of the segments are linked by the echo train length (ETL) via the Equation (1) described above, wherein A is chosen equal to the echo train length.

The echo train length (which is also called Turbo Factor in TSE) specifies the number of k-space lines (or the number of echoes) that are read out after an excitation pulse and is normally an additional parameter to be provided by the user. In order to be able to implement an SMS measurement, it must thus be ensured that the SMS requirements (Equations (2) and (4)) are satisfied even after a modification of the aforementioned parameters by the operator or by experts. Since those parameters which must be individually adapted for each patient (in particular the extent of the predetermined volume segment in the phase coding direction—"Phase FOV") also belong among the cited parameters, a parameter set that is established once cannot always be used.

The parameters are automatically adapted via the present invention (in particular the method according to the invention that is shown in FIG. 3) such that the user advantageously neither has to care about parameter dependencies for the SMS technique nor has to know about these dependencies. This saves on special training of the operator, shortens the examination workflow, and avoids operating errors.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to control acquisition of magnetic resonance data in a magnetic resonance system, comprising the steps of:
   storing procedure parameters that define a sliding multi-slice (SMS) data acquisition procedure having data acquisition requirements that must be satisfied when acquiring magnetic resonance data with said SMS data acquisition procedure;
   from said computerized control unit, operating a magnetic resonance data acquisition unit to acquire magnetic resonance data from a predetermined volume segment of an examination subject according to said SMS data acquisition procedure by executing a plurality of repetitions of said SMS data acquisition procedure and, in each repetition, exciting nuclear spins in, and reading resulting magnetic resonance signals from, a number of slices in said predetermined volume segment while continuously longitudinally moving the examination subject on a patient table in a longitudinal direction through said data acquisition unit; and
   exclusively in said computerized control unit, automatically determining said number of slices, in which nuclear spins are excited and from which resulting magnetic resonance signals are read in each repetition, from at least one of said procedure parameters, in order to satisfy said data acquisition requirements of said SMS data acquisition procedure, with no manual designation of said number of slices to said computerized control unit, by entering the magnetic resonance data read from each slice into a number, of k-space segments, that is at least two k-space segments, and comprising, in said computerized control unit, automatically determining said number of slices dependent on the number of k-space segments per slice.

2. A method as claimed in claim 1 comprising, from said computerized control unit, causing said number of slices to be visually displayed at a display unit.

3. A method as claimed in claim 1 comprising, in said computerized control unit, selecting said procedure parameters for determining said number of slices from the group of procedure parameters consisting of image contrast and image resolution.

4. A method as claimed in claim 1 wherein each of said k-space segments comprises a selectable number of k-space lines in which said magnetic resonance data are entered, and comprising, in said computerized control unit, automatically determining the number of k-space lines in each segment dependent on at least one procedure parameter, among said procedure parameters that define said SMS data acquisition procedure, selected from the group consisting of image contrast and image resolution and, dependent on said number of k-space lines in each segment, automatically also determining, in said computerized control unit, at least one further procedure parameter, selected from the group consisting of said number of slices in each repetition, a speed of said longitudinal movement of said patient table, and a total number of said repetitions to acquire all magnetic resonance data from said predetermined volume segment.

5. A method as claimed in claim 4 comprising automatically determining, in said computerized control unit, a minimum total number of k-space lines for each slice dependent on said at least one procedure parameter of said SMS data acquisition procedure and also automatically determining, in said computerized control unit, a total number of k-space lines for each slice as an integer multiple of said number of k-space lines per segment that is greater than or equal to said minimum total number of k-space lines.

6. A method as claimed in claim 5 comprising, in said computerized control unit, automatically determining a number of additional k-space lines from a difference between said total number of k-space lines and said minimum total number of k-space lines, and using said additional k-space lines to modify entry of said magnetic resonance data into k-space by a modification selected from the group consisting of reducing a line interval in k-space while maintaining unchanged a distance of outermost k-space lines from the center of k-space, entering data into a central region of k-space with increased data entry density, and repeatedly entering data into at least some of said k-space lines.

7. A method as claimed in claim 4 comprising, in said computerized control unit, automatically determining said number of segments per slice according to $$S = \frac{N_{PE}}{A},$$

wherein S is the number of segments per slice, $N_{PE}$ is a total number of k-space lines per slice, and A is the number of k-space lines per segment.

8. A method as claimed in claim 7 comprising setting A in said computerized control unit to a value selected from the group consisting of an echo train length of said magnetic resonance signals, and a manual input to said computerized control unit.

9. A method as claimed in claim 7 comprising setting $N_{PE}$ in said computerized control unit dependent on a value selected from the group consisting of a time required for acquisition of said magnetic resonance data for each slice, and a speed of said movement of said patient table.

10. A method as claimed in claim 7 comprising, in said computerized control unit, automatically determining said number of slices in which nuclear spins are excited and from which resulting magnetic resonance signals are read in each repetition according to $$N = p \times S,$$

wherein N is said number of said slices, p is a predetermined factor, and S is the number of segments per slice.

11. A method as claimed in claim 10 comprising, in said computerized control unit, determining, from said SMS data acquisition procedure, whether directly adjacent slices, among said number of slices, are excited in immediate succession or not, and setting said factor p equal to 1 when directly adjacent slices are excited in immediate succession, and setting said factor p equal to 2 when directly adjacent slices are not excited in immediate succession.

12. A method as claimed in claim 10 comprising, in said computerized control unit, automatically determining said number of repetitions of said SMS data acquisition procedure according to $$N_{REP} = r \times \left( \frac{L}{p \times d} + (S-1) \right),$$

wherein L is a length of said predetermined volume segment in said longitudinal direction of movement of said patient table, d is a slice interval, r is a number of repetitions of said SMS data acquisition procedure necessary for complete acquisition of said magnetic resonance data from said predetermined volume segment and $N_{REP}$ is said number of repetitions.

13. A method as claimed in claim 12 comprising, from said computerized control unit, causing said predetermined volume segment to be graphically displayed at a display unit and designating said length of said predetermined volume segment into the computerized control unit from the graphical display of said predetermined volume segment.

14. A method as claimed in claim 12 comprising generating a localizer image of said examination subject, that includes said predetermined volume segment, and designating said length of said predetermined volume segment into said computerized control unit from said localizer image.

15. A method as claimed in claim 12 comprising determining said length of said predetermined volume segment in said computerized control unit as a product of said number of slices and said slice interval.

16. A method as claimed in claim 10 comprising controlling, from said computerized control unit, a speed of said movement of said patient table and setting said speed $v_{table}$ according to $$v_{table} = \frac{p \times d}{TS},$$

wherein d is a slice interval and TS is a time span in which said magnetic resonance data are acquired from each segment.

17. A method as claimed in claim 10 comprising, in said computerized control unit, determining N and setting a slice interval d so that a product of N and d is equal to a length of an active volume in the longitudinal direction of said movement of the patient table, said active volume being a volume in a center of said data acquisition unit, in which said number of slices are located while exciting said nuclear spins therein and reading the resulting magnetic resonance signals therefrom.

18. A method as claimed in claim 1 comprising terminating repetition of said SMS data acquisition procedure as soon as a last slice within said predetermined volume segment exits, due to said movement of said patient table, an active volume in a center of said data acquisition unit.

19. A method as claimed in claim 1 comprising, from said computerized control unit, operating said data acquisition unit to satisfy at least one boundary condition selected from the group consisting of said number of slices being less than or equal to a total number of slices that are capable of being excited, encoded and read out in a repetition interval of said SMS data acquisition procedure, a speed of said movement of said table is less than or equal to a predetermined maximum table speed and an active volume in a center of said data acquisition unit is smaller than or equal to a volume within said data acquisition unit in which a predetermined magnetic field homogeneity and a predetermined gradient line exits.

20. A device to control acquisition of magnetic resonance data in a magnetic resonance system, comprising:
a memory in which procedure parameters are stored that define a sliding multi-slice (SMS) data acquisition procedure having data acquisition requirements that must be satisfied when acquiring magnetic resonance data with said SMS data acquisition procedure;
a computerized control unit configured access said memory to operate a magnetic resonance data acquisition unit to acquire magnetic resonance data from a predetermined volume segment of an examination subject according to said SMS data acquisition procedure by executing a plurality of repetitions of said SMS data acquisition procedure and, in each repetition, exciting nuclear spins in, and reading resulting magnetic resonance signals from, a number of slices in said predetermined volume segment while continuously longitudinally moving the examination subject on a patient table through said data acquisition unit; and
said computerized control unit being configured to automatically determine, exclusively in said computerized control unit, said number of slices, in which nuclear spins are excited and from which resulting magnetic resonance signals are read in each repetition, from at least one of said procedure parameters, in order to satisfy said requirements for acquisition of magnetic resonance data with said SMS data acquisition procedure, with no manual designation of said number of slices to said computerized control unit, by entering the magnetic resonance data read from each slice into a number, of k-space segments, that is at least two k-space segments, and comprising, in said computerized control unit, automatically determining said number of slices dependent on the number of k-space segments per slice.

21. A device as claimed in claim 20 comprising a display unit and wherein said computerized control unit is configured to cause said number of slices to be visually displayed at said display unit.

22. A device as claimed in claim 20 comprising wherein said computerized control unit is configured to select said parameters for determining said number of slices from the group of procedure parameters consisting of image contrast and image resolution.

23. A device as claimed in claim 20 wherein each of said k-space segments comprises a selectable number of k-space lines in which said magnetic resonance data are entered, and wherein said computerized control unit is configured to automatically determine the number of k-space lines in each segment dependent on procedure parameters, among said procedure parameters that define said SMS data acquisition procedure, selected from the group consisting of image contrast and image resolution and, dependent on said number of k-space lines in each segment, to automatically also determine at least one further parameter selected from the group consisting of said number of slices in each repetition, a speed of said longitudinal movement of said patient table, and a total number of said repetitions to acquire all magnetic resonance data from said predetermined volume segment.

24. A device as claimed in claim 23 wherein said computerized control unit is configured to automatically determine a minimum total number of k-space lines for each slice dependent on said at least one parameter of said SMS data acquisition procedure and to also automatically determine a total number of k-space lines for each slice as an integer multiple of said number of k-space lines per segment that is greater than or equal to said minimum total number of k-space lines.

25. A device as claimed in claim 24 wherein said computerized control unit is configured to automatically determine a number of additional k-space lines from a difference between said total number of k-space lines and said minimum total number of k-space lines, and to use said additional k-space lines to modify entry of said magnetic resonance data into k-space by a modification selected from the group consisting of reducing a line interval in k-space while maintaining unchanged a distance of outermost k-space lines from the center of k-space, entering data into a central region of k-space with increased data entry density, and repeatedly entering data into at least some of said k-space lines.

26. A device as claimed in claim 23 wherein said computerized control unit is configured to automatically determine said number of segments per slice according to $$S = \frac{N_{PE}}{A},$$

wherein S is the number of segments per slice, $N_{PE}$ is a total number of k-space lines per slice, and A is the number of k-space lines per segment.

27. A device as claimed in claim 26 wherein said computerized control unit is configured to set a value selected from the group consisting of an echo train length of said magnetic resonance signals, and a manual input to said computerized control unit.

28. A device as claimed in claim 26 wherein said computerized control unit is configured to set $N_{PE}$ computerized control unit dependent on a value selected from the group consisting of a time required for acquisition of said magnetic resonance data for each slice, and a speed of said movement of said patient table.

29. A device as claimed in claim 26 wherein said computerized control unit is configured to automatically determine said number of slices in which nuclear spins are excited and from which resulting magnetic resonance signals are read in each repetition according to $$N=p=S,$$

wherein N is said number of said slices, p is a predetermined factor, and S is the number of segments per slice.

30. A device as claimed in claim 29 wherein said computerized control unit is configured to determine, from said SMS data acquisition procedure, whether directly adjacent slices, among said number of slices, are excited in immediate succession or not, and to set said factor p equal to 1 when directly adjacent slices are excited in immediate succession, and to set said factor p equal to 2 when directly adjacent slices are not excited in immediate succession.

31. A device as claimed in claim 29 wherein said computerized control unit is configured to automatically determine said number of repetitions of said predetermined data acquisition procedure according to $$N_{REP} = r \times \left( \frac{L}{p \times d} + (S-1) \right),$$

wherein L is a length of said predetermined volume segment in said longitudinal direction of movement of said patient table, d is a slice interval, r is a number of repetitions of said SMS data acquisition procedure necessary for complete acquisition of said magnetic resonance data from said predetermined volume segment and $N_{REP}$ is said number of repetitions.

32. A device as claimed in claim 31 comprising a display unit and wherein said computerized control unit is configured to cause said predetermined volume segment to be graphically displayed at said display unit and to allow designation of said length of said predetermined volume segment into the computerized control unit from the graphical display of said predetermined volume segment.

33. A device as claimed in claim 31 wherein said computerized control unit is configured to operate said data acquisition unit to generate a localizer image of said examination subject, that includes said predetermined volume segment, and to allow designation of said length of said predetermined volume segment into said computerized control unit from said localizer image.

34. A device as claimed in claim 31 wherein said computerized control unit is configured to determine said length of said predetermined volume segment as a product of said number of slices and said slice interval.

35. A device as claimed in claim 20 wherein said computerized control unit is configured to control a speed of said movement of said patient table and to set said speed $v_{table}$ according to $$v_{table} = \frac{p \times d}{TS},$$

wherein d is a slice interval and TS is a time span in which said magnetic resonance data are acquired from each segment.

36. A device as claimed in claim 20 wherein said computerized control unit is configured to determine said number of slices N and to set a slice interval d so that a product of N and d is equal to a length of an active volume in the longitudinal direction of said movement of the patient table, said active volume being a volume in a center of said data acquisition unit, in which said number of slices are located while exciting said nuclear spins therein and reading the resulting magnetic resonance signals therefrom.

37. A device as claimed in claim 20 wherein said computerized control unit is configured to terminate repetition of said data acquisition procedure as soon as a last slice within said predetermined volume segment exits, due to said movement of said patient table, an active volume in a center of said data acquisition unit.

38. A device as claimed in claim 20 wherein said computerized control unit is configured to operate said data acquisition unit to satisfy at least one boundary condition selected from the group consisting of said number of slices being less than or equal to a total number of slices that are capable of being excited, encoded and read out in a repetition interval of said SMS data acquisition procedure, a speed of said movement of said table is less than or equal to a predetermined maximum table speed and an active volume in a center of said data acquisition unit is smaller than or equal to a volume within said data acquisition unit in which a predetermined magnetic field homogeneity and a predetermined gradient line exits.

39. A magnetic resonance apparatus comprising:
a magnetic resonance data acquisition unit;

a memory in which procedure parameters are stored that define a sliding multi-slice (SMS) data acquisition procedure having data acquisition requirements that must be satisfied when acquiring magnetic resonance data with said SMS data acquisition procedure;

a computerized control unit configured to operate a magnetic resonance data acquisition unit to acquire magnetic resonance data from a predetermined volume segment of an examination subject according to said SMS data acquisition procedure by executing a plurality of repetitions of said SMS data acquisition procedure and, in each repetition, exciting nuclear spins in, and reading resulting magnetic resonance signals from, a number of slices in said predetermined volume segment while continuously longitudinally moving the examination subject on a patient table through said data acquisition unit; and said computerized control unit being configured to automatically determine, exclusively in said computerized control unit, said number of slices, in which nuclear spins are excited and from which resulting magnetic resonance signals are read in each repetition, from at least one of said procedure parameters, in order to satisfy said data acquisition requirements of said SMS data acquisition procedure, with no manual designation of said number of slices to said computerized control unit, by entering the magnetic resonance data read from each slice into a number, of k-space segments, that is at least two k-space segments, and comprising, in said computerized control unit, automatically determining said number of slices dependent on the number of k-space segments per slice.

40. A non-transitory computer-readable medium encoded with programming instructions, said medium being loadable into a computerized control system of a magnetic resonance apparatus, that also includes magnetic resonance data acquisition unit, and said programming instructions causing said computerized control system to:

store procedure parameters that define a sliding multi-slice (SMS) data acquisition procedure having data acquisition requirements that must be satisfied when acquiring magnetic resonance data with said SMS data acquisition procedure;

operate the magnetic resonance data acquisition unit to acquire magnetic resonance data from a predetermined volume segment of an examination subject according to said SMS data acquisition procedure by executing a plurality of repetitions of said SMS data acquisition procedure and, in each repetition, excite nuclear spins in, and read resulting magnetic resonance signals from, a number of slices in said predetermined volume segment while continuously longitudinally moving the examination subject on a patient table through said data acquisition unit; and exclusively in said computerized control system, automatically determine said number of slices, in which nuclear spins are excited and from which resulting magnetic resonance signals are read in each repetition, from at least one of said procedure parameters, in order to satisfy said data acquisition requirements of said SMS data acquisition procedure, with no manual designation of said number of slices to said computerized control system, by entering the magnetic resonance data read from each slice into a number, of k-space segments, that is at least two k-space segments, and comprising, in said computerized control unit, automatically determining said number of slices dependent on the number of k-space segments per slice.

41. A method to control acquisition of magnetic resonance data in a magnetic resonance system, comprising the steps of:

storing a predetermined data acquisition procedure in a computerized control unit, said predetermined data acquisition procedure being defined by procedure parameters;

from said computerized control unit, operating a magnetic resonance data acquisition unit to acquire magnetic resonance data from the predetermined volume segment of an examination subject according to said predetermined data acquisition procedure by executing a plurality of repetitions of said data acquisition procedure and, in each repetition, exciting nuclear spins in, and reading resulting magnetic resonance signals from, a number of slices in said predetermined volume segment while continuously longitudinally moving the examination subject on a patient table in a longitudinal direction through said data acquisition unit;

exclusively in said computerized control unit, automatically determining said number of slices, in which nuclear spins are excited and from which resulting magnetic resonance signals are read in each repetition, from at least one of said procedure parameters, with no manual designation of said number of slices to said computerized control unit; and from said computerized control unit, operating said data acquisition unit to satisfy at least one boundary condition selected from the group consisting of said number of slices being less than or equal to a total number of slices that are capable of being excited, encoded and read out in a repetition interval of said data acquisition procedure, a speed of said movement of said table is less than or equal to a predetermined maximum table speed and an active volume in a center of said data acquisition unit is smaller than or equal to a volume within said data acquisition unit in which a predetermined magnetic field homogeneity and a predetermined gradient linearity exits.

42. A device to control acquisition of magnetic resonance data in a magnetic resonance system, comprising:

a memory in which a predetermined data acquisition procedure is stored, said predetermined data acquisition procedure being defined by procedure parameters;

a computerized control unit configured to operate a magnetic resonance data acquisition unit to acquire magnetic resonance data from the predetermined volume segment of an examination subject according to said predetermined data acquisition procedure by executing a plurality of repetitions of said data acquisition procedure and, in each repetition, exciting nuclear spins in, and reading resulting magnetic resonance signals from, a number of slices in said predetermined volume segment while continuously longitudinally moving the examination subject on a patient table through said data acquisition unit;

said computerized control unit being configured to automatically determine, exclusively in said computerized control unit, said number of slices, in which nuclear spins are excited and from which resulting magnetic resonance signals are read in each repetition, from at least one of said procedure parameters, with no manual designation of said number of slices to said computerized control unit; and said computerized control unit being configured to operate said data acquisition unit to satisfy at least one boundary condition selected from the group consisting of said number of slices being less than or equal to a total number of slices that are capable of being excited, encoded and read out in a repetition interval of said data acquisition procedure, a speed of said movement of said table is less than or equal to a predetermined maximum table speed and an active volume in a center of said data acquisition unit is smaller than or equal to a volume within said data acquisition unit in which a predetermined magnetic field homogeneity and a predetermined gradient linearity exits.

43. A magnetic resonance apparatus comprising:

a magnetic resonance data acquisition unit;

a memory in which a predetermined data acquisition procedure is stored, said predetermined data acquisition procedure being defined by procedure parameters;

a computerized control unit configured to operate a magnetic resonance data acquisition unit to acquire magnetic resonance data from the predetermined volume segment of an examination subject according to said predetermined data acquisition procedure by executing a plurality of repetitions of said data acquisition procedure and, in each repetition, exciting nuclear spins in, and reading resulting magnetic resonance signals from, a number of slices in said predetermined volume segment while continuously longitudinally moving the examination subject on a patient table through said data acquisition unit;

said computerized control unit being configured to automatically determine, exclusively in said computerized control unit, said number of slices, in which nuclear spins are excited and from which resulting magnetic resonance signals are read in each repetition, from at least one of said procedure parameters, with no manual designation of said number of slices to said computerized control unit; and said computerized control unit being configured to operate said data acquisition unit to satisfy at least one boundary condition selected from the group consisting of said number of slices being less than or equal to a total number of slices that are capable of being excited, encoded and read out in a repetition interval of said data acquisition procedure, a speed of said movement of said table is less than or equal to a predetermined maximum table speed and an active volume in a center of said data acquisition unit is smaller than or equal to a volume within said data acquisition unit in which a predetermined magnetic field homogeneity and a predetermined gradient linearity exits.

44. A non-transitory computer-readable medium encoded with programming instructions, said medium being loadable into a computerized control system of a magnetic resonance apparatus, that also includes magnetic resonance data acquisition unit, and said programming instructions causing said computerized control system to:

store a predetermined data acquisition procedure, said predetermined data acquisition procedure being defined by procedure parameters;

operate the magnetic resonance data acquisition unit to acquire magnetic resonance data from the predetermined volume segment of an examination subject according to said predetermined data acquisition procedure by executing a plurality of repetitions of said data acquisition procedure and, in each repetition, excite nuclear spins in, and read resulting magnetic resonance signals from, a number of slices in said predetermined volume segment while continuously longitudinally moving the examination subject on a patient table through said data acquisition unit;

exclusively in said computerized control system, automatically determine said number of slices, in which nuclear spins are excited and from which resulting magnetic resonance signals are read in each repetition, from at least one of said procedure parameters with no manual designation of said number of slices to said computerized control system; and operate said data acquisition unit to satisfy at least one boundary condition selected from the group consisting of said number of slices being less than or equal to a total number of slices that are capable of being excited, encoded and read out in a repetition interval of said data acquisition procedure, a speed of said movement of said table is less than or equal to a predetermined maximum table speed and an active volume in a center of said data acquisition unit is smaller than or equal to a volume within said data acquisition unit in which a predetermined magnetic field homogeneity and a predetermined gradient linearity exits.

\* \* \* \* \*